(12) United States Patent
Al-Thallab

(10) Patent No.: US 11,234,989 B2
(45) Date of Patent: Feb. 1, 2022

(54) METHOD FOR DIAGNOSING AND TREATING BRONCHIAL ASTHMA

(71) Applicant: Fatema Salem Al-Thallab, Jahra (KW)

(72) Inventor: Fatema Salem Al-Thallab, Jahra (KW)

(*) Notice: Subject to any disclaimer, the term of this patent is extended or adjusted under 35 U.S.C. 154(b) by 410 days.

(21) Appl. No.: 16/295,664

(22) Filed: Mar. 7, 2019

(65) Prior Publication Data

US 2019/0201415 A1    Jul. 4, 2019

Related U.S. Application Data

(63) Continuation of application No. 11/765,521, filed on Jun. 20, 2007, now abandoned.

(51) Int. Cl.
| | | |
|---|---|---|
| *A61K 31/137* | (2006.01) | |
| *A61P 11/06* | (2006.01) | |
| *A61K 31/56* | (2006.01) | |

(52) U.S. Cl.
CPC .................................. *A61K 31/56* (2013.01)

(58) Field of Classification Search
CPC .............................. A61K 31/137; A61P 11/06
USPC ......................................................... 514/653
See application file for complete search history.

(56) References Cited

U.S. PATENT DOCUMENTS

| | | |
|---|---|---|
| 3,109,773 A | 11/1963 | Mercer et al. |
| 5,215,965 A | 6/1993 | Lezdey et al. |
| 6,620,428 B1 | 9/2003 | Hoeck et al. |
| 2007/0197499 A1 | 8/2007 | Del Soldato |

OTHER PUBLICATIONS

Tanizaki et al., Yoshiro, "A New Modified Classification of Bronchial Asthma Based on Clinical Symptoms," Journal of Internal Medicine, vol. 32, No. 3, Mar. 1993, pp. 197-203.
"Clinical Practice Guidelines, Expert Panel Report 2, Guidelines for the Diagnosis and Management of Asthma" National Institutes of Health, National Heart, Lung and Blood Institute, NIH Publication No. 97-4051, Jul. 1997.
Tanizaki et al., Yoshiro, "Type 11 (bronchiolar obstruction) asthma and number of neutrophils in bronchoalveolar lavage (BAL) flu id," et al.. vol. 46 (4), pp. 295-301, 1992.
Hough et al., Alexandra, "Physiotherapy in respiratory care: an evidence-based approach to respiratory and cardiac management, Third Edition," Nelson Thornes Ltd, Delta Place, 27 Bath Road, Cheltenham, Glos., GL53 7th, United Kingdom, 2001.
Lougheed et al., M. Diane, "Dynamic Hyperinflation During Bronchoconstriction in Asthma: Implications for Symptom Perception," Chest, vol. 130, No. 4, Oct. 2006.

*Primary Examiner* — Raymond J Henley, III
(74) *Attorney, Agent, or Firm* — Nath, Goldberg & Meyer; Richard C. Litman

(57) ABSTRACT

A method for diagnosing and treating a bronchial asthma by classifying a patient's asthma as Type I, Type II or Type III based on the patient's symptoms is disclosed. The symptoms for the three types of asthma are disclosed together with recommended treatment guidelines for each type to optimize treatment regiments based on symptoms.

1 Claim, 4 Drawing Sheets

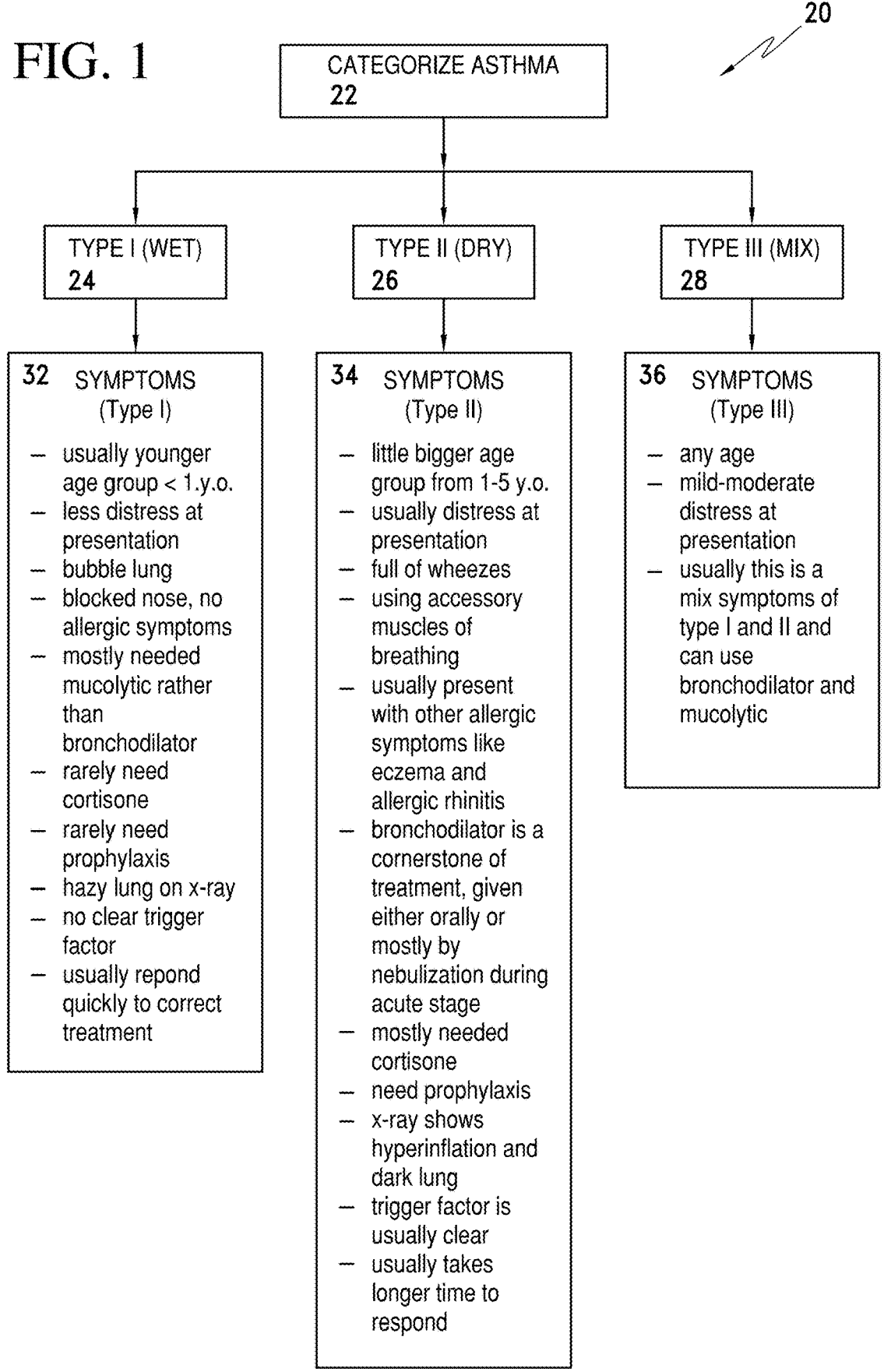

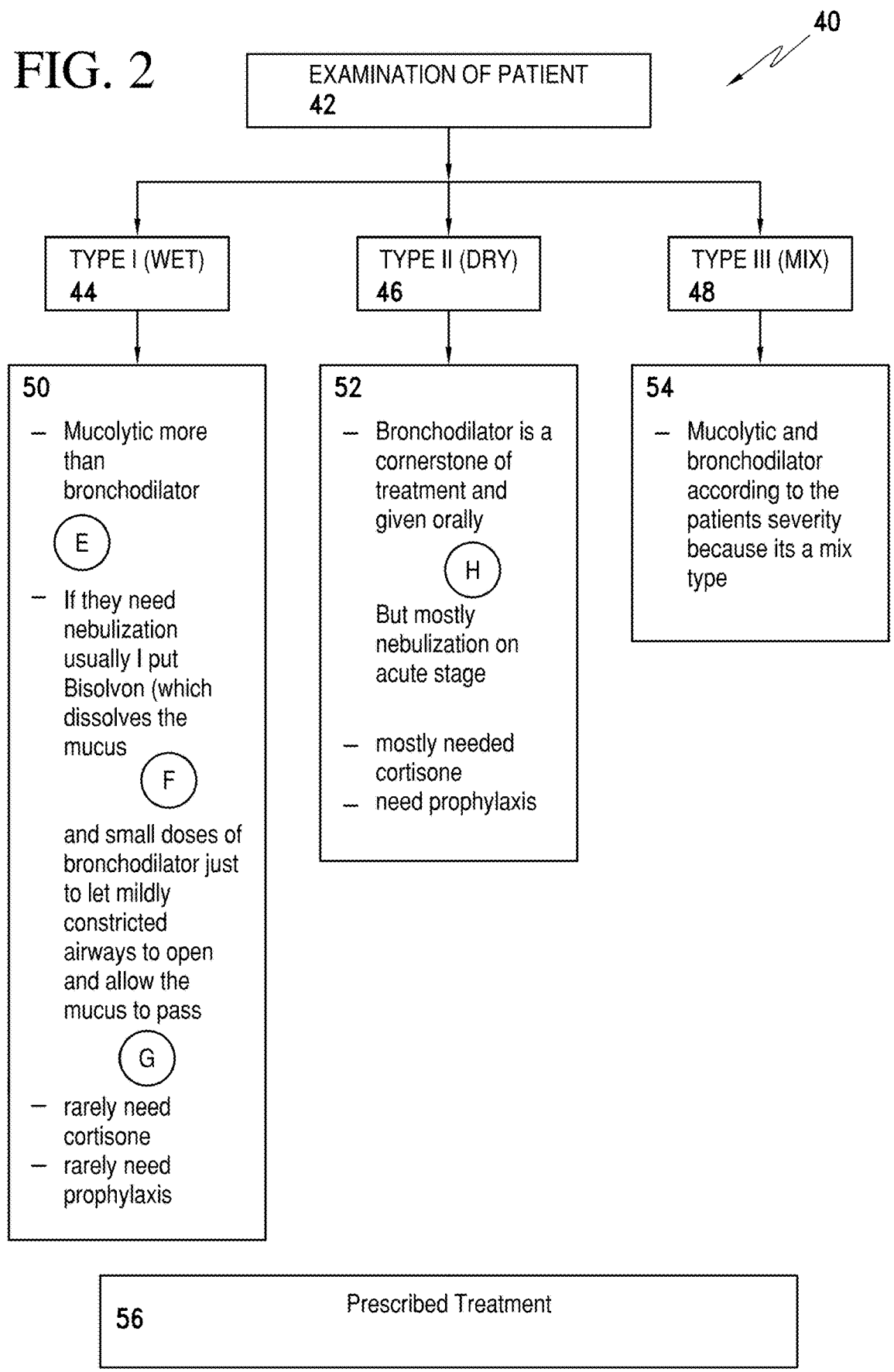

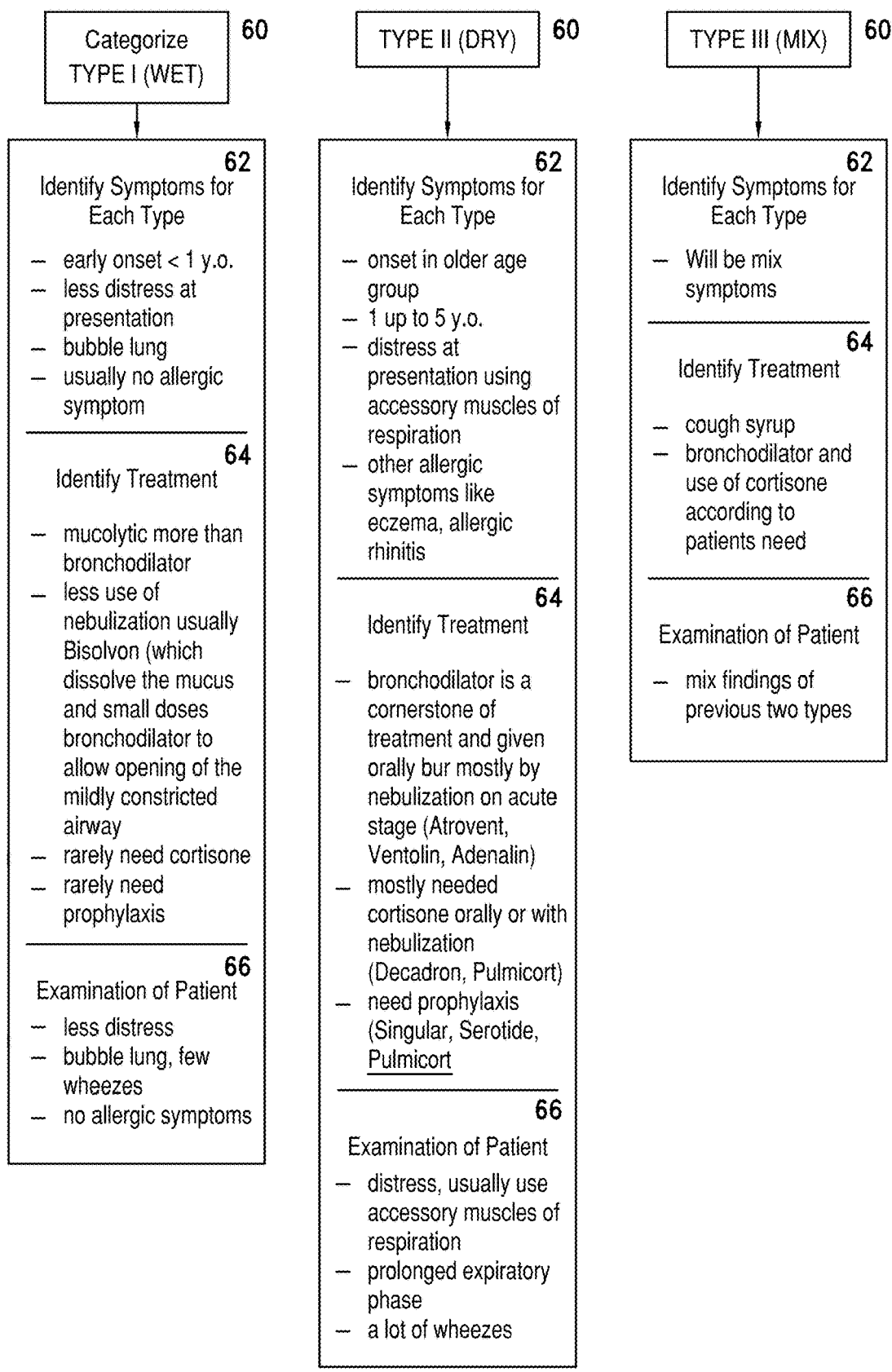

FIG. 4

68 Prescribed Treatment

— ordinary treatment will be bronchodilator and cough suppressor
— may give cortisone

70 Evaluate the Result

— if the baby use the ordinary treatment we are not hitting the main pathology which is predominance of mucus so he is taking usually unnecessary chemical drugs. On the other hand, the main pathology is production of mucus which needs drug to dissolve it and it needed mild bronchodilator to open the constricted bronchioles so that the mucus will be expelled. But if we give bronchodilator alone it will not get the mucus out and the condition will recur — less use of cortisone becuase there is mild bronchoconstriction — less use of prophylaxis since the main pathology is treated which is mucus production

68 Prescribed Treatment

— cough suppressor
— bronchodilator either orally or by nebulization
— cortisone
— prophylaxis

70 Evaluate the Result

— compared to regular classic treatment of asthma, I added small doses of Adrenalin (epinephrine) and inhaled steroid which gave excellent result and ended by less or nearly quick response (mind that this medical treatment is already available in the market), I only categorize them to the right patient

68 Prescribed Treatment

— its a mixed, mucolytic and bronchodilator according to patients needs

70 Evaluate the Result

— This type is mix so the patient will use bronchodilator and mucolytic in equal amount
— Chances of using prophylaxis and cortisone is also the same

METHOD FOR DIAGNOSING AND TREATING BRONCHIAL ASTHMA

CROSS REFERENCE TO RELATED APPLICATIONS

This application is a continuation of application Ser. No. 11/765,521, filed Jun. 20, 2007, now abandoned.

FIELD OF THE INVENTION

This invention relates to a method for diagnosing and treating bronchial asthma and more particularly to a method and treatment based on categorizing bronchial asthma into three types and optimizing treatment based on the type of asthma encountered.

BACKGROUND FOR THE INVENTION

It has been reported that asthma is the number one chronic illness for children and is a significant cause of infants' deaths. It has also been reported that over twenty million Americans have asthma. It addition, it is well known that asthma is adversely affected by pollution. For this reason, there has been a significant increase in asthma cases in Kuwait since the Gulf War and the fire set in the Kuwait oil fields by the retreating Iraqi troops.

Bronchial Asthma typically causes decreased lung function, bronchial inflammation, coughing, wheezing and tightness in the chest. These problems are often exasperated by air born irritants such as smoke, exercise, viral infections etc. When a patient encounters such problems, it means that the individual's airway is obstructed and the lungs are not receiving sufficient air. Typically, the airways become obstructed due to the lining of the airways becoming irritated and swollen and because the airways tighten causing them to narrow.

With modern medicine, there are many treatments for asthma. However, most of the drugs prescribed have the potential for negative side effects. For example, asthma treatment can cause depression, dizziness, fatigue, impotence, liver damage etc. In addition, some medications are effective for some patients but less effective with others. Therefore, it is highly desirable to select the right treatment for the right patient.

The main idea of the new invention is to categorize the patient with Bronchial Asthma so you can give the right medication to the right patient thereby reducing side effects of the medication.

BRIEF SUMMARY OF THE INVENTION

In essence the present invention contemplates a method for diagnosing and treating a patient with Bronchial Asthma. The method includes the step of classifying a patient's asthma into three types, namely Type I (a wet type), Type II (a dry type) and Type III (a mixed type). The Type I asthma is characterized by more production of mucus than bronco constriction while the dry type has more bronco spasm than mucus production. The mixed type is a mixture of the two i.e. Type I and Type II. A patient is then diagnosed as Type I, Type II or Type III based on an examination of the patient. For Type I, a patient is treated with a mucolyptic more than a bronco dilator or with a bronco dilator if Type II or some combination of the two if Type III.

In a preferred embodiment of the invention, the diagnosis is based on the onset of symptoms, severity of symptoms at the onset of the symptoms, chest findings, other allergy symptoms, X-ray findings, trigger factors and to a degree response to treatment and age of the patient. The treatment for the Type I asthma includes more use of a mucolyptic than a broncho dilator, and if a nebulizer is used it should include Bisolvon®, a bromhexine that is a synthetic derivative of vasicine. In essence the Bisolvon® is an expectorant i.e. mucus or phlem dissolving preparation. Small doses of a bronco dilator may also be used to open the passages to let the mucus pass. Cortisone is seldom used for such patients.

For those patients with the Type II asthma, they are treated with a bronco dilator and/or nebulizer with the addition of Atrovert, adrenaline and pulmicort if needed in measured amounts. This combination has given relatively quick response and is often effective in decreasing the use of a nebulizer. The treatment for Type III includes a combination of the treatments for Types I and II and is derived based on the physician's experience.

DESCRIPTION OF THE DRAWINGS

FIG. 1 a block diagram illustrating a method for categorizing different types of asthma in accordance with the present invention;

FIG. 2 is a block diagram illustrating a method for treating different types of asthma in accordance with the present invention;

FIG. 3 is a block diagram illustrating a method for diagnosing and treating asthma in accordance with the present invention; and FIG. 4 is a block diagram illustrating the method for diagnosing and treating asthma in accordance with the present invention.

DESCRIPTION OF THE PREFERRED EMBODIMENTS OF THE INVENTION

A diagnostic method and method for treating patients with Bronchial Asthma will now be described in connection with FIGS. 1-3. As illustrated in FIG. 1, a diagnostic method 20 includes a step 22 of dividing or categorizing asthma into three types i.e. Type I (wet type) as indicated by box 24, Type II (dry type) as indicated by box 26 and Type III (mixed type) as indicated by box 28. The division of the three types is based on differences in symptoms.

The criteria for diagnosing the different types of asthma were developed based on the examination and treatment of numerous patients. The criteria are based on the age of the patient, the age at initial attack (onset of the presentation) or the severity of the initial attack(s), chest findings, evidence of other symptoms as well as the results of any previous treatments tried and used.

Differences in chest findings for the different types of Bronchial Asthma are described as follows: Type I (wet type)—chest examination will reveal a bubbled sound, Type II (dry type)—there will be flaring of alae nasi, and using accessory muscles of respiration, prolonged expiratory phase and wheezes and in Type III (mixed type), we could find the mixture of symptoms of both types.

Evidences of other symptoms are likewise outlined here. In Wet Type I, the baby will usually present with a blocked nose, less likely to have allergic symptoms and cough throughout the day. In Dry Type II, the child will be very distress, manifesting allergic symptoms like allergic rhinitis, eczema which may precede or come later and continuous cough throughout the day but usually more severe during the night.

To expound further on the result of any previous treatment tried and used, it is understood that Bronchial Asthma was not recognized before as a heterogenous disease thus it was treated as only one disease using cough syrup and a bronchodilator. Although some authors were against giving mucolytics, some others were giving mucolytics because it was not clear to them that Bronchial Asthma is not just one disease. As some were against, others may be giving mucolytic with a bronchodilator. Most of available medications for treatment of Bronchial Asthma is recategorize according to the types of Bronchial Asthma and this gives good results because the right treatment id given to the right patient.

Before the new invention, all kinds of bronchial asthma were treated the same and it is divided into its Acute Stages:

During Acute Stage:
For a child in acute stage:
1. mostly nebulizer
    Bronchodilator—mainly Ventolin (6) and Atrovent (3) use of mucolytic like Bisolvon (1) was controversial.
    Inhaled Steroid—less likely to be used, its used mainly as a prophylaxis.
2. Injected Steroid—can be used if the case needed.
3. Some authors add IV aminophylline (7) which is not currently recommended.
4. Once the Acute Stage passes they gave:
    Bronchodilator like Ventolin (6) syrup or Bricanyl (8) or Berotec (9) and some used oral cortisone.

As Prophylaxis:
This is decided according to severity, age of patient and available medication
1. Either Pulmicort (5) or Flixotide (10) inhaler (inhaled steroid)
2. Singular (11)—either sachet 4 mg or 4-5 mg label These were what were used to be given before for all children with Bronchial Asthma but with the new invention:

The Wet Type:
During Acute Stage:
Need more mucolytic to dissolve the mucus like Bisolvon (1) and you can add bronchodilator to help open the closed bronchioles
If you do so you will not need to use cortisone either inhaled or injectable. When the Acute Stage subsides, I will give any mucolytic like Mucosolvan (12) and Prospan (13) to dissolve the sputum which will give dramatic and marvelous result. This group of patient since you treated the cause they're less likely to get prophylaxis The Dry Type:
During Acute Stage:
Inhalation: Use Ventolin (6) Nebulization Solution, Adrenalin (4) and inhaled Steroid like Pulmicort (5) No need for inhaled mucolytic
Some need to be given injectable steroids and they gave dramatic response
Once patient's acute stage subsides, I will give cough syrup and bronchodilator like Bricanyl (8)+/− oral cortisone (2)
This group of patient may need prophylaxis either inhaled steroid or singular In addition to the above X-ray findings, trigger factors and responses to further treatment are considered. The following are the usual x-ray findings:
In Wet Type:—the x-ray wil be hazy, white lung
In Dry Type:—signs of hyperinflation, and a dark lung The Type I asthma sometimes referred to as the Wet Type and is typically characterized by the following symptoms as indicated by box 32. The symptoms include the age of the patient. For example, Type I asthma is typically found in younger patients from 0 to 1 year old. The type I asthma is also characterized by less distress during an attack (presentation) and chest findings that show bubbled lungs, few wheezes during an attack and lack of allergic symptoms. Additional symptoms include the finding that the patient rarely need prophylactics like Singular (11) if needed and their x-rays show a hazy white lung field. Further, there are no clear triggering factors and the patient usually shows a relatively quick response to proper treatment for Type I asthma.

The symptoms for Type II asthma are typically found in an older age group i.e. those are usually from 1 to 5 years of age but can also occur later on and are further characterized by prolonged expiratory phases and lots of wheezes. Additional symptoms of the Type II asthma relate to the use of accessory muscles for breathing and evidence of other allergies.

A number of patients that exhibit evidence of both Type I and Type II asthma are categorized as Type III i.e. a Mixed Type of asthma. Unless patients' symptoms that are predominantly categorized as Type I or Type II they are classified as a Type III or mixed type asthmatic. Usually the following symptoms occur for the Dry Type II patients; severe distress on presentation, flaring alae nasi, using accessory muscles of respiration, with or without cyanosis, inability to continue the sentences spoken, cough mainly at night, runny nose and could be preceded by a viral infection, exercise and they could also have eczema.

Having characterized the types of asthma and the symptoms of each type, a physician is better prepared to examine and treat a patient, which is defined as a treatment method 40. In the treatment method 40, a physician reviews a patient's medical history and examines the patient and conducts a conventional examination of the patient in step 42. After examining the patient, the physician characterizes the patient's asthma as Type I in box 44, Type II in box 46 or Type III as indicated by box 48. After characterizing the type of asthma experienced by the patient in boxes 44, 46 and 48, the physician considers the appropriate treatment as set forth in boxes 50, 52 and 54 and prescribes an appropriate regime for the patient as indicated by box 56.

5 The treatment for Type I Asthma includes the use of mucolytic such as Mucosolvan (12), Prospan (13), Bisolvon (1) and Tuscalman (14) more so than bronchodilators. Bronchodilators which acts as mainstay on nebulization are Ventolin (6) and Atrovent (3). In those cases where a nebulizer is called for, an addition of Bisolvon (1) (bromhexine or its equivalent) to dissolve the mucus may be added based on the physician's experience. The physician may also add small doses of a bronchodilator such as Atrovent (3) and Ventolin (6) to let the mildly constricted airways open up and let the mucus pass. In Type I asthma, cortisone is rarely used as re prophylactics.

Hypothetical Patient: Type I
Mariam is 2 months of age with weight of 5.4 kg, height 52 cm and presented with cough, noisy breathing and blocked nose for the last 3 days after her father smoke cigarettes near the baby. She was afebrile, mildly distress on examination, no cyanosis, respiratory rales is mildly distress and no dysmorphic feature.
  Mouth: oral trash
  Ear: no abnormality detected
  Nose: blocked
  Chest: bubbled lung, no wheezes
  Abdomen: intact CVS: intact CNS: intact Baby was diagnosed to have Bronchial Asthma Type I. She was given the following treatment:

Tuscalman (14)

Prospan drops (13)

The treatment of Type II asthma typically includes the use of a bronchodilator as a cornerstone of treatment. Such bronchodilators may be administered orally but mostly by nebulizers particularly in an acute stage. These bronchodilators are given either thru nebulization such as Atrovent (3), Ventolin (6) or Adrenalin (4) or as orally using Bricanyl (8), Berotec (9) or Ventolin (6). Cortisones may also be used through inhalation using Pulmicort (5) and oral steroid such as Decadron (2). Prophylactics used for this type are inhaled steroid and Singular (11).

An example of a Hypothetical patient having Type II asthma and their treatment follows:

Hypothetical Case, Type II

Mosa is a 5 year old boy, he was presented to my clinic with distress, severe cough that he could not sleep last night after he was exposed to a sandstorm. Last night, the child is restless with flaring alae nasi, using his accessory muscles or respiration, mildly cyanotic, afebrile, HR (100/min), high RR and a congested throat Chest—prolonged expiratory phase a lot of wheezes Others—system intact He was given hydrocortisone injection with a dose of 50 mg new nebulization are Atrovent (3) and Pulmicort (5) with Adrenalin (4). He was diagnosed to have attacks of Bronchial Asthma, Type II (Dry Type) he was given cough syrup.

Bronchodilator in nebulization for 2-3 days followed by oral Bronchodilator like Bricanyl (8) or Berotec (9) and cortisone (Decadron) (2). This boy used to have a frequent attacks of Bronchial Asthma. Last attack was before 2 weeks so he needs to take prophylaxis like Singular (11) tablets or Pulmicort (5) nebulization solution according to the discussion with the mother.

The treatment of Type III asthma presents a greater challenge to the physician. With symptoms of Type I and Type II asthma present, it is necessary to use a balance treatments from each type and find a treatment that fits the need of a specific patient. For example, a treatment of a hypothetical patient based on a compilation of studies of patients with Type III asthma is as follows:

Hypothetical Case Type III

Mohesen is 1.2 month old boy who was presented with a cough and running nose for one week. Clinical presentation mild to moderate distress, afebrile, chest findings is a mix of bubble lung and wheezes. He took 2 doses of nebulization (Atrovent (3), Ventolin (6)) and continued a bronchodilator and cough syrup like Sinecod (15).

The practice of a preferred embodiment of the present invention will now be described in connection with FIG. 3. As shown in FIG. 3, a physician characterizes the three types of asthma as indicated in box 60 based on the symptoms for each of the three types as indicated in box 62. The physician also identifies the treatment which were generally most effective for each of the three types of asthma as indicated by box 64. As indicated by box 66, with the above mental background, the physician conducts a conventional examination of a patient including review of the patient's medical history and prescribes an appropriate treatment as indicated by box 68. Following this, the physician follows up on the results of the treatment as indicated in box 70 and if necessary modifies the treatment.

Drug Index

1. Bisolvon (Bromhexine Hydrochloride)—
   Mucolytics
   Concentration: 4 mg/2 ml for inhalation and oral administration containing 8 mg
   Bromhexine is a synthetic derivative of a herbal active ingredient vasicine
   Enhances mucous transport by reducing mucous viscosity, mucociliary clearance

| Doses: Children | 6-12: 1 ml 2 times daily |
   | --- | --- |
   | | 2-6: 10 drops 2 times daily |
   | | <2.yo: 5 drops 2 times daily |

But usually we add 2-3 drops which is more than enough

2. Decadron (Dexamethasone)
   A synthetic glucocorticoid used for its anti-inflammatory effects
   It has 25 to 30 times the anti-inflammatory activity of hydrocortisone
   0.5 mg tablet: blister pack of 30's, 0.5 mg/5 ml: bottle of 100 ml as elixir
   Doses: In acute, self-limited allergic disorders or acute exacerbations of chronic allergic disorders (e.g. bronchial asthma)
   Dosage requirements are variable and must be individualized according to the severity of the disease and the response of the patient
   The usual initial dosage varies from 0.75 to 15 mg a day depending on the disease being treated
   For infants and children, the recommended doses usually will have to be reduced, but dosage should be dictated by the severity of the condition rather than by age or body weight.)

3. Atrovent (Ipatroplum Bromide)
   Anti muscarinic bronchodilator
   Doses of child: 100-500 microgram (0.4-2 ml at 0.02% solution)
   1 ml (20 drops) 0.025% solution for inhalation with nebulising devices contain: 261 mcgg (=1 ipatropium bromide) corresponding to 250 mg ipatropium bromide anhydrose bronchodilator
   Doses 6-12 years old: 1 ml (20 drops=0.25 ml) 3 to 4 times daily <6 y.o.: 0.4-1 ml (8-20 drops=0.1-0.25 mg) 3 to 4 times daily 4. Adrenalin—

5. Pulmicort Nebulizer Solution (Budesonide)
   Concentration: 0.25 mg/ml-0.5 mg/ml
   Budesonide is a gluco corticosteroid with a high local anti inflammatory effect to prevent the release of inflammatory mediator
   Studies have shown that the earlier budesonide treatment is initiated after the onset of asthma, the better lung function can be expected
   Doses:
   Acute: from 6 months: 0.25-0.5 mg per day, may increase up to 1 mg/day
   Prophylaxis: from 6 months: 0.25-2 mg/day 6. Ventolin Respiratory Solution
   Provide 5 mg/ml of salbutamol sulphate of nebulization
   It is selective Beta 2 agonist that provides short acting (4-6 ml) bronchodilator with fast onset (5 miniutes)
   Dose in children under the age of 12 years old Minimum: 0.5 ml (2.5 mg of salbutamol) diluted to 2-2.5 ml with normal saline
However, higher dose of up to 5 mg could be used 7. Aminophylline—
8. BRICANYL (Terbutaline Sulphate)
   1 ml contains Terbutaline sulphate 0.3 mg
   Should be used as a maintenance therapy in asthma ans other pulmonary diseases where bronchospasm is a complicating factor
   Doses: Children: 0.075 mg (0.25 ml)/kg Body weight 3 times daily
   Suitable Doses: (Kg) Dosage

| (Kg) | Dosage |
|---|---|
| 4 | 1 ml × 3 |
| 6 | 1.5 ml × 3 |
| 8 | 2 ml × 3 |
| 10 | 2.5 ml × 3 |
| 12 | 3 ml × 3 |
| 14 | 3.5 ml × 3 |
| 16 | 4 ml × 3 |
| 18 | 4.5 ml × 3 |
| 20 | 5 ml × 3 |
| 24 | 6 ml × 3 |
| 28 | 7 ml × 3 |
| 32 | 8 ml × 3 |
| 36 | 9 ml × 3 |
| 40 | 10 ml × 3 |

If an adequate response is not obtained with this dose, the dose may be doubled, provided adverse reactions are not pronounced 9. Berotec
   Bronchodilator
   2.5 mg tablet, liquid 2.5 mg 5 ml
   Iteaspoonful liquid contains 1-(3,5-dihydroxyphenyl)-2-(hydroxy-benzyl)-ethyl-amino athanol hydrobromide (=fenoterol hydrobromide)
   Doses:
     Infants up to 1 y.o.—(below 10 kg BW)=2.5 ml liquid 2 to 3 times daily Children 1-6 y.o—(ca. 10-22 kg BW)=0.5-1 tablet/2.5-5 ml liquid 3× daily Children 6-14 y.o.—=1 tablet or 5 ml liquid 3 times dail
10. Flixotide Evohaler 125 Mcg
    Fllixotide Evohaler is a pressurized inhalation, suspension delivering 125 micrograms of fluticasone propionate per actuation
    Given by inhalation offers offers prophylactic treatment of asthma
      Doses: Mild Asthma:—100 to 250 mcgs twice daily
      Moderate Asthma:—250 to 500 mcgs twice daily
      Severe Asthma:—500 to 1,000 mcgs twice daily
      Administration of doses >1000 mcgs (500 mcgs twice daily) should be via spacer device to help reduce side-effects in the mouth and throat
    The dose should be titrated to the lowest dose t which effective control of asthma is maintained
    It should be taken regularly even when asymptomatic. Onset of therapeutic effect is within 4 to 7 days
11. Singular (Montelukast Sodium)
    4 mg sachet, 4 mg, 5 mg chewable tablet
    It is a leukotriene receptor antagonist so it blocks the receptos of leukotriene (naturally occurring chemicals that cause narrowing of the airway and inflammation)
    Doses: From 6 months-5 years=4 mg either sachet or chewable tablet
    From 6-12 years=5 mg once daily or at bedtime
12. Mucosolvan
    Preclinically, ambroxol, the active ingredianet of Mucosolvan, has been shown to increase respiratory tract secretion. It enhances pulmonary surfactant production and stimulate ciliary activity
    liquid 15 mg/5 ml, solution for oral or inhalation use 15 mg/2 ml
    Doses:
      Liquid 15 mg/5 ml
      <2 y.o.—2.5 ml (½ teaspoon) 2 times daily
      2-6 y.o.—2.5 ml (½ teaspoon) 3 times daily
      6-12 y.o.—5 ml (1 teaspoon) 2-3 times daily
      Solution 15 mg/2 ml for oral and inhalation use
      <2 y.o.—1 ml (=25 drops) 2 times daily
      2-6 y.o.—1 ml (=25 drops) 3 times daily
      >6 y.o.—2 ml (=50 drops) 2-3 times daily
13. Prospan (Herbal Drops)
    Mucolytic, spasmolytic, cough relieving
    100 ml bottle
    Composition: 100 ml solution contains 2 g of dried ivy leaf extract (5-7.5:1); extractive agent: ethanol 30% (w/w): Herbal Drops contains 47% vol. alcohol
    Herbal Drops is a natural product and contains an active ingredient which is purely herbal
    Doses: Infants—10 to 15 drops 3 to 5 times daily
      Small children—15 drops 3 to 5 times daily
      Adults and schoolchildren—20 drops 3 to 5 times daily
14. Tuscalman
    Antitussive
    Tuscalman contains noscapine as the effective principle. This substance exerts a reliable, suppressive action on the cough center
    Drops: 15 mg Noscapini Hydrochloridium, 100 mg Guaifenesinum Syrup: 15 mg, 100 mg, 250 mg
    Suppositories: 10 mg, 50 mg
    Packings: 20 ml dropper-bottle, 120 ml bottle,
    Suppositories A and B=boxes of 10 suppositories
    Doses:
      Drops for Children—10-20 drops for 2 to 3 times daily
      Syrup: 6-12 y.o.—1 teaspoonful 3 to 5 times daily
      Suppositories A:—0-8 months 2 suppositories daily
        9-18 months 3 suppositories daily
      Suppositories B:—1.5 to 3 y.o—2 suppositories daily
        4-8 y.o.—3 to 4 suppositories daily
15. Sinecod
    Antitussive
    Active Principle: Butamirate citrate, a central cough suppressant which is chemically and pharmacologically unrelated to the opium alkaloids. It reduce airway resistance
    Drops for children: pack of 20 ml, syrup: pack of 200 ml
    Doses: Drops for Children: 2 months—1 year—10 drops 4 times daily
      1-3 y.o.—15 drops 4 times daily
      <3 y.o.—25 drops 4 times daily
      Syrup: 3 to 6 y.o.—5 ml 3 times daily
      6 to 12 y.0.—10 ml 3 times daily While the invention has been described in connection with its preferred embodiment it should be recognized that changes and modifications can be made therein without departing from the scope of the appended claims.

What is claimed is:

1. A method of treating bronchial asthma, comprising:
   categorizing symptoms of bronchial asthma in a child patient by wet type, dry type, or mixed type;
   orally administering a principal dose of mucolytic with a dose of bronchodilator to a wet type patient, administering a bronchodilator, cough suppressor, adrenaline, and inhaled steroid to a dry type patient, and administering principal doses of both mucolytic and bronchodilator to the mixed type patient; and administering a prophylactic anti-inflammatory treatment to the dry type patient.

* * * * *